(12) United States Patent
Chowdhury et al.

(10) Patent No.: US 7,271,174 B2
(45) Date of Patent: **\*Sep. 18, 2007**

(54) METABOLITES OF TRICYCLIC AMIDES USEFUL FOR INHIBITION OF G-PROTEIN FUNCTION AND METHODS OF TREATMENT OF PROLIFERATIVE DISEASES

(75) Inventors: Swapan K. Chowdhury, Warren, NJ (US); Anima Ghosal, Edison, NJ (US); Robert M. Iannucci, Basking Ridge, NJ (US); Wenqing Feng, Edison, NJ (US); Tze-Ming Chan, Bridgewater, NJ (US); Shmuel Zbaida, East Brunswick, NJ (US); Kevin B. Alton, Cedar Knolls, NJ (US); Ronald J. Doll, Convent Station, NJ (US); Keith P. Minor, Dallas, TX (US)

(73) Assignee: Schering Corporation, Kenilworth, NJ (US)

( * ) Notice: Subject to any disclaimer, the term of this patent is extended or adjusted under 35 U.S.C. 154(b) by 54 days.

This patent is subject to a terminal disclaimer.

(21) Appl. No.: 10/874,556

(22) Filed: Jun. 23, 2004

(65) Prior Publication Data

US 2004/0266810 A1    Dec. 30, 2004

Related U.S. Application Data

(60) Provisional application No. 60/482,373, filed on Jun. 25, 2003.

(51) Int. Cl.
*C07D 221/06*    (2006.01)
*A61K 31/435*   (2006.01)

(52) U.S. Cl. .................... 514/290; 546/93
(58) Field of Classification Search .......... 546/93; 514/290
See application file for complete search history.

(56) References Cited

U.S. PATENT DOCUMENTS

| | | | |
|---|---|---|---|
| 5,874,442 A * | 2/1999 | Doll et al. .......... | 514/290 |
| 6,358,968 B1 | 3/2002 | Remiszewski et al. | |
| 6,575,639 B2 | 6/2003 | Shibutani | |
| 2001/0039283 A1 | 11/2001 | Cooper et al. | |

FOREIGN PATENT DOCUMENTS

| | | |
|---|---|---|
| WO | WO95/00497 | 1/1995 |
| WO | WO95/10516 | 4/1995 |

OTHER PUBLICATIONS

67 USPQ 2d 1664 Aug. 2003, Schering Corp V Geneva Pharmaceuticals Inc.*

Int'l Search Report Dec. 16, 2004.
Liu, Ming, et. al., "Anititumor Activity of SCH 66336 . . .", Cancer Research, vol. 58, pp. 4947-4956 (1998).

* cited by examiner

*Primary Examiner*—Rita Desai
(74) *Attorney, Agent, or Firm*—Gerard E. Reinhardt

(57) ABSTRACT

The present invention relates to metabolites of tricyclic amides, and structurally related compounds, represented by the structural formula (I):

and pharmaceutically acceptable isomers, salts, solvates or esters of the compound of formula (I), wherein:

$R_1$ is selected from the group consisting of H and =O;

$R_2$-$R_5$ can be the same or different, each being independently selected from the group consisting of H, —OH, halide, —$NH_2$ and =O; and, the combination solid-dashed lines independently represent either single bonds or double bonds, wherein the number of combination solid-dashed lines that are double bonds is not greater than 2, and when, the double bonds are not adjacent, and when 0, one of $R_1$-$R_5$ is not H.

Also disclosed are methods of treatment of proliferative diseases and methods for inhibiting the abnormal growth of cells, and for inhibiting farnesyl protein transferase using the novel compounds.

7 Claims, No Drawings

METABOLITES OF TRICYCLIC AMIDES USEFUL FOR INHIBITION OF G-PROTEIN FUNCTION AND METHODS OF TREATMENT OF PROLIFERATIVE DISEASES

CROSS-REFERENCE TO RELATED APPLICATION

This application claims the benefit under 35 U.S.C. §119(e) of U.S. provisional application Ser. No. 60/482,373, filed Jun. 25, 2003, which is incorporated by reference herein as if fully set forth.

BACKGROUND

FIELD OF THE INVENTION

Some embodiments of the present invention relate to metabolites of tricyclic amides useful for inhibition of G-protein function, to related compounds and to methods of treatment of proliferative diseases.

The biological significance of the rat sarcoma ("Ras") oncogene, and the roles of both Ras and the enzyme known as farnesyl protein transferase ("FPT") in the conversion of normal cells to cancer cells, are described in PCT International Publication Nos. WO95/00497 and WO95/10516. Each of those publications also describes a distinct class of compounds which inhibit the activity of the enzyme farnesyl protein transferase, and thereby the farnesylation of the Ras protein.

In U.S. Pat. No. 5,874,442, which is incorporated by reference herein in its entirety, a number of tricyclic amide compounds useful in the inhibition of farnesyl protein transferase are disclosed. Among these compounds is the following, which is herein referred to as "Compound A":

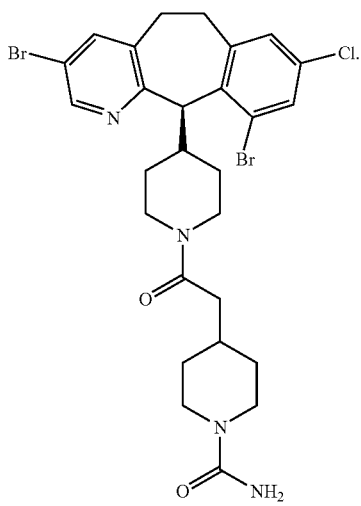

A

Compound A is particularly useful in the inhibition of farnesyl protein transferase. The administration of an effective amount of this compound provides a method for inhibiting the abnormal growth of cells, including transformed cells, and for treatment of cancers, as described in U.S. Pat. No. 5,874,442.

SUMMARY OF THE INVENTION

In some embodiments, the present invention is directed to compounds represented by the structural formula (I):

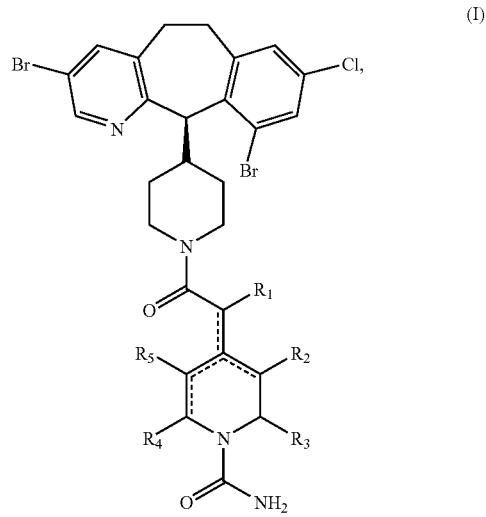

(I)

and pharmaceutically acceptable isomers, salts, solvates or esters of the compound of formula (I), wherein:
  $R_1$ is selected from the group consisting of H and =O;
  $R_2$-$R_5$ can be the same or different, each being independently selected from the group consisting of H, —OH, halide, —$NH_2$ and =O; and,
  the combination solid-dashed lines independently represent either single bonds or double bonds, wherein the number of combination solid-dashed lines that are double bonds is not greater than 2, and when 2, the double bonds are not adjacent, and when 0, one of $R_1$-$R_5$ is not H.

In some embodiments, the present invention is directed to compounds represented by the structural formula (I), wherein $R_1$, $R_2$, $R_3$, and $R_5$ are each H, $R_4$ is selected from the group consisting of H and —OH, and the number of combination solid-dashed lines that are double bonds is not greater than 1.

In some embodiments, the present invention is directed to a compound represented by the structural formula

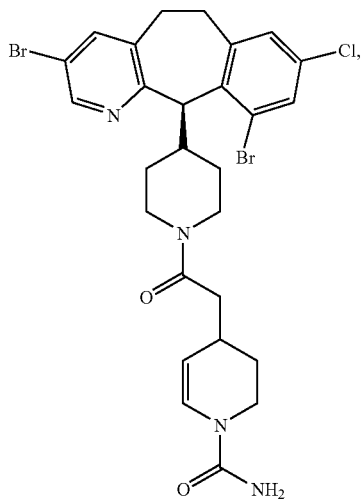

and pharmaceutically acceptable isomers, salts, solvates or esters thereof. In a further embodiment, the invention is directed to a pure and isolated form of the above compound.

In some embodiments, the present invention is directed to a compound represented by the structural formula

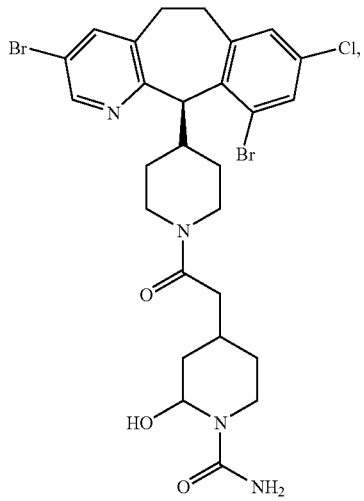

and pharmaceutically acceptable isomers, salts, solvates or esters thereof. In a further embodiment, the invention is directed to a pure and isolated form of the above compound.

In some embodiments, the present invention is directed to a compound represented by the structural formula

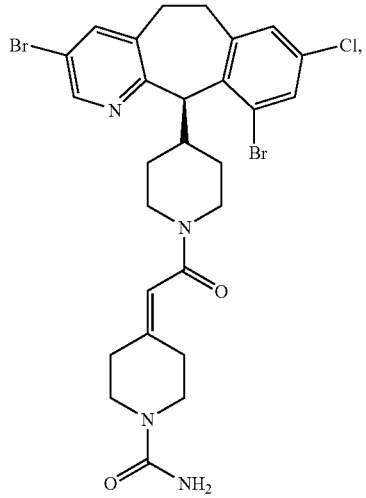

and pharmaceutically acceptable isomers, salts, solvates or esters thereof. In a further embodiment, the invention is directed to a pure and isolated form of the above compound.

In some embodiments, the present invention is directed to a compound represented by the structural formula

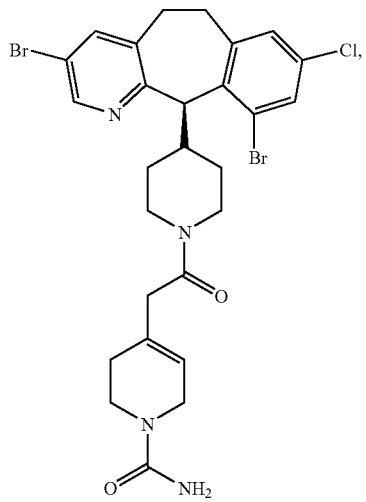

and pharmaceutically acceptable isomers, salts, solvates or esters thereof. In a further embodiment, the invention is directed to a pure and isolated form of the above compound.

In some embodiments, the present invention is directed to a method of inhibiting farnesyl protein transferase in a patient in need of such inhibition comprising administering a therapeutically effective amount of at least one of a compound of formula (I).

In some embodiments, the present invention is directed to a method of treating pancreatic cancer, non-small cell lung cancer, myeloid leukemia, thyroid follicular cancer, myelodysplastic syndrome, epidermal carcinoma, bladder carcinoma, colon cancer, breast cancer or prostate cancer in a patient in need of such treatment comprising administering a therapeutically effective amount of at least one compound of formula (I).

In some embodiments, the present invention is directed to a pharmaceutical composition comprising a therapeutically effective amount of at least one compound of formula (I) in combination with a pharmaceutically acceptable carrier.

In some embodiments, the present invention is directed to pure and isolated forms of the compounds of formula (I).

DETAILED DESCRIPTION OF INVENTION

In certain embodiments, the present invention is directed to metabolites of the Compound A which can: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and/or (iv) block abnormal cell growth in culture induced by transforming Ras. The following four compounds (labeled Compounds 8-11) are metabolites of Compound A:

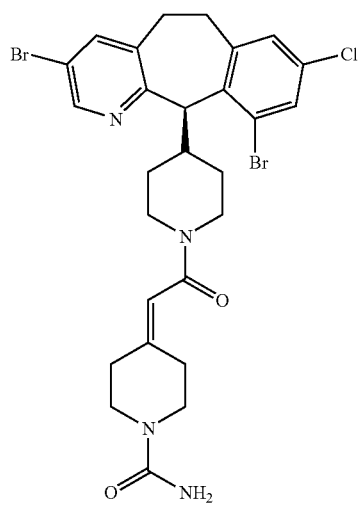

8

-continued

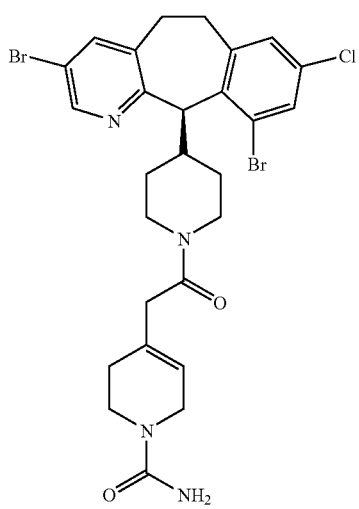

9

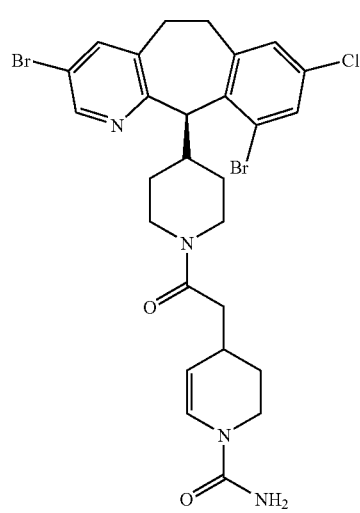

10

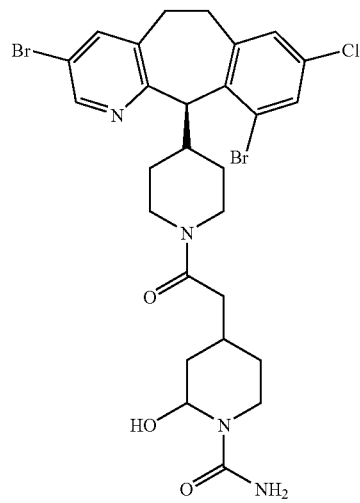

11

Compound A has been demonstrated to have anti-tumor activity in animal models, and thus its metabolites are of corresponding utility.

The present invention is further directed to compounds that are structurally similar to the metabolites of the Compound A, and are believed to have corresponding utility. Such structurally related compounds are represented by the structural formula (I):

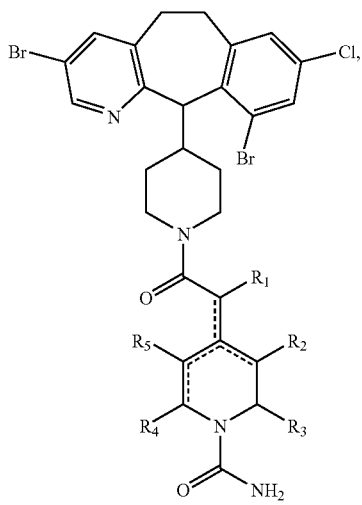

wherein:
$R_1$ is selected from the group consisting of H and $=O$;
$R_2$-$R_5$ can be the same or different, each being independently selected from the group consisting of H, —OH, halide, —$NH_2$ and $=O$; and,
the combination solid-dashed lines independently represent either single bonds or double bonds, wherein the number of combination solid-dashed lines that are double bonds is not greater than 2, and when 2, the double bonds are not adjacent, and when 0, one of $R_1$-$R_5$ is not H.

This invention includes the above compounds in the amorphous state or in the crystalline state.

This invention provides a method for inhibiting the abnormal growth of cells, including transformed cells, by administration of a therapeutically effective amount of at least one of the compounds of formula (I), to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting tumor growth by administration of a therapeutically effective amount of at least one of the compounds of formula (I), to a mammal (e.g., a human) in need of such treatment. In particular, this invention provides a method for inhibiting the growth of tumors expressing an activated Ras oncogene by the administration of an effective amount of one of the above-described metabolites. Examples of tumors which may be inhibited include, but are not limited to, lung cancer (e.g., lung adenocarcinoma and non-small cell lung cancer), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (e.g., acute myelogenous leukemia (AML)), thyroid follicular cancer, myelodysplastic syndrome (MDS), bladder carcinoma, epidermal carcinoma, breast cancers and prostate cancers.

This invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of a therapeutically effective amount of at least one of the compounds of formula (I) to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn) may be inhibited by the metabolites of the invention.

The metabolites of this invention inhibit farnesyl protein transferase and the farnesylation of the oncogene protein Ras. This invention further provides a method of inhibiting Ras farnesyl protein transferase in mammals, especially humans, in need of such treatment by the administration of an effective amount of at least one of the compounds of formula (I). The administration of at least one of the compounds of formula (I) to patients to inhibit farnesyl protein transferase can be useful in the treatment of the cancers described above.

The compounds useful in the methods of this invention inhibit the abnormal growth of cells. Without wishing to be bound by theory, it is believed that these compounds may function through the inhibition of G-protein function, such as Ras p21, by blocking G-protein isoprenylation, thus making them useful in the treatment of proliferative diseases such as tumor growth and cancer. Without wishing to be bound by theory, it is believed that these compounds inhibit Ras farnesyl protein transferase, and thus show antiproliferative activity against Ras transformed cells.

Also, the compounds of formula (I) can have utility in other methods of treatment by that involve the inhibition of farnesyl protein transferase. Additional conditions and diseases treatable by the administration of compounds that inhibit farnesyl protein transferase are disclosed in U.S. provisional application 60/498,509, which is herein incorporated by reference as if fully set forth.

Salts of the compounds of formula (I) are also within the scope of this invention. Reference to a compound of formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization. Salt-forming acids within the scope of the present invention include hydrochloride, sulfate, hydrobromide, tartrate, mesylate, maleate, citrate, phosphate, acetate, pamoate/embonate, hydroiodide, nitrate, lactate, methylsulfate and fumarate. Salt-forming bases within the scope of the present invention include sodium, calcium, potassium, magnesium, meglumine, ammonium, aluminum, zinc, piperazine, tromethamine, lithium, choline, diethylamine, 4-phenylcyclohexylamine and benzathine.

All isomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual isomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the inventive compounds.

It should also be noted that any carbon as well as heteroatom with unsatisfied valences in the text, schemes, examples and Tables herein is assumed to have the sufficient number of hydrogen atom(s) to satisfy the valences.

As used above, and throughout the specification, the following terms, unless otherwise indicated, shall be understood to have the following meanings:

"Patient" includes both human and animals.

"Mammal" means humans and other mammalian animals.

"Halogen" means fluorine, chlorine, bromine, or iodine. "Halo" or "halide" means fluoro, chloro, bromo, or iodo groups.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula (I) or a salt and/or solvate thereof. A discussion of prodrugs is provided in T. Higuchi and V. Stella, *Pro-drugs as Novel Delivery Systems*, Volume 14 of the A.C.S. Symposium Series (1987) and in *Bioreversible Carriers in Drug Design*, Edward B. Roche, ed., American Pharmaceutical Association and Pergamon Press (1987), both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules is incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting farnesyl protein transferase, and thus producing the desired therapeutic effect.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

With reference to the number of moieties (e.g., substituents, groups or rings) in a compound, unless otherwise defined, the phrase "not greater than two" means 0, 1 or 2. The phrase "not greater than one" means 0 or 1.

The above statements wherein, for example, "$R_2$-$R_5$ can be the same or different, each being independently selected from the group consisting of H, —OH, halide, —$NH_2$ and =O" mean that the selection of each named substituent, i.e., $R_2$, $R_3$, $R_4$ and $R_5$, is independent from the selection of any other substituent in the group. Thus, for example the selection of $R_2$ to be H would be independent of the selection of $R_3$, which could be —OH, in the same molecule.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine ($Et_3N$); diethyl ether ($Et_2O$); ethyl chloroformate ($ClCO_2Et$); 1-(3-dimethylaminopropyl)-3-ethyl carbodiimde hydrochloride (DEC); diisobutylaluminum hydride (DIBAL); isopropanol (iPrOH); dimethylsulfoxide (DMSO); sodium dodecyl sulfate (SDS); trichloroacetic acid (TCA); dithiothreitol (DTT); tris(hydroxymethyl)aminomethane (tris); and ethylenediaminetetraacetic acid (EDTA).

Unless otherwise indicated, all quantitative measures of physical parameters stated herein, e.g., temperature, mass, volume, concentration, are understood to include a reasonable scope of variation from the stated quantity.

The compounds of the present invention can be prepared by the procedures described below.

EXAMPLE 1

Preparation of Compounds 8 and 9

Step 1

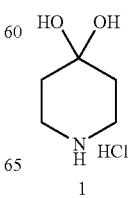 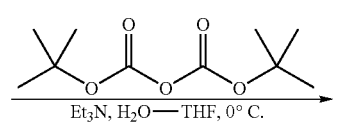

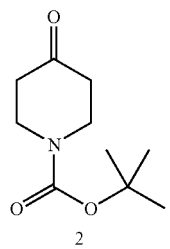

According to a procedure by Labouta et al. (Labouta, A. M. et al., *Eur. J. Med. Chem.-Chem. Therm.*, vol. 17, no. 6, pp. 531-535, (1982)), 4-piperidone hydrate hydrochloride, 1, (20.0 g, 130 mmol), was dissolved in H₂O (100 mL). Triethylamine (58 mL, 417 mmol, 3.2 equiv) was added, followed by a solution of di-tert-butyl dicarbonate (39.8 g, 182 mmol, 1.4 equiv) in THF (100 mL) at 0° C. The solution was stirred overnight (0° C.→RT). The reaction mixture was then concentrated under vacuum, and the residue was purified by silica gel chromatography (10:1 hexanes-ethyl acetate) to afford 24.0 g (93%) of tert-Butyl 4-piperidone-1-carboxylate (076483-141-26; CAS 79099-07-3), Compound 2, as a colorless oil. A small amount of di-tert-butyl dicarbonate remained in the product (by ¹H NMR), but the material was of suitable purity to carry to the following step.

Step 2

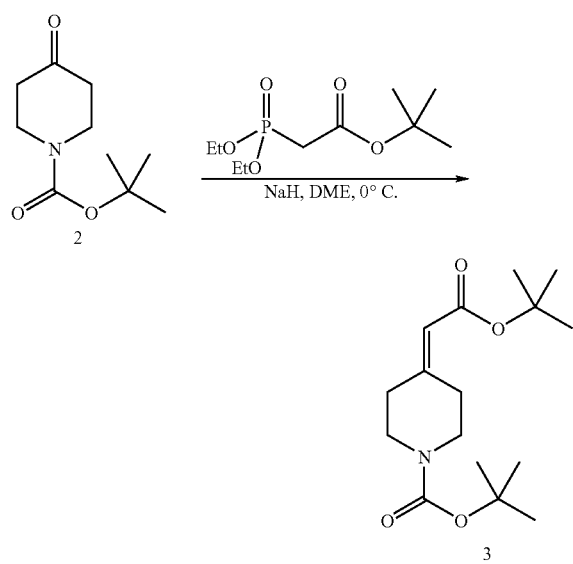

Also according to the procedure by Labouta et al., tert-butyl diethylphosphonoacetate (15.0 g, 59.6 mmol, 1.2 equiv) in dry 1,2-dimethoxyethane (50 mL) was added dropwise to a suspension of NaH (60% dispersion in mineral oil, unwashed, 2.38 g, 59.6 mmol, 1.2 equiv) in dry 1,2-dimethoxyethane (150 mL) at 0° C. After stirring Compound 2 for 0.5 h, tert-butyl 4-piperidone-1-carboxylate (9.9 g, 49.7 mmol) in dry 1,2-dimethoxyethane (20 mL) was added dropwise to the mixture at 0° C., and then stirred overnight (0° C.→RT). The reaction was then quenched with NaHCO₃ (100 mL, saturated aqueous), and the layers were separated. The aqueous phase was extracted with CH₂Cl₂ (3×20 mL), and the combined organic phase was dried (MgSO₄), filtered, then concentrated under vacuum. The residue was purified by silica gel chromatography (95:5 hexanes-ethyl acetate) to afford 10.2 g (69%) of tert-Butyl 1-tert-butoxy-carbonylpiperidin-4-ylideneacetate (076483-143-32; CAS 84839-55-4), Compound 3, as a colorless oil.

Step 3:

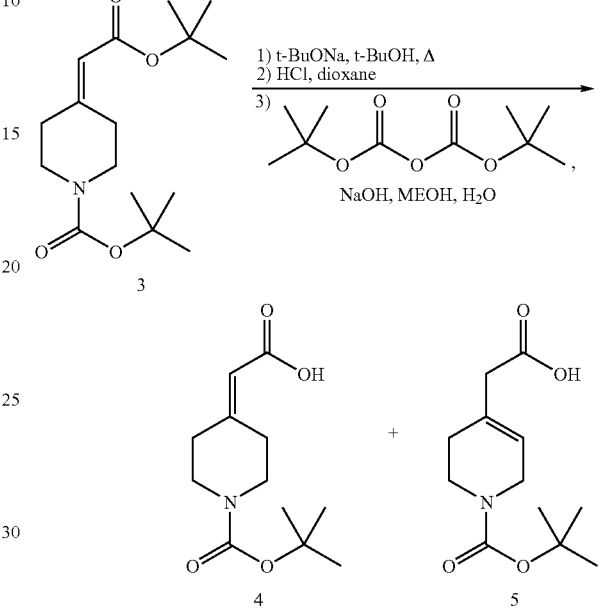

Tert-Butyl 1-tert-butoxycarbonylpiperidin-4-ylideneacetate, Compound 3, (10.2 g, 34.2 mmol) was dissolved in a solution of t-BuONa (1.6 g, 0.5 equiv) in dry t-BuOH (150 mL). The equilibration was carried at 100° C. for 0.5 h, then at RT overnight. NH₄Cl (saturated aqueous) was then added to pH =7, and the solution was extracted with hexanes (2×20 mL), followed by extraction with CH₂Cl₂ (4×20 mL). The combined organic phase was dried (MgSO₄), filtered, then concentrated under vacuum. The residue, a mixture of Compounds 4 and 5, 1-tert-Butoxycarbonylpiperidin-4-ylideneacetic Acid and 1-tert-butoxycarbonyl-1,2,5,6-tetrahydropyridineacetic Acid (076483-149-30, respectively), was taken to the next step without further purification.

The residue was dissolved in CH₂Cl₂ (20 mL) and a solution of HCl in 1,4-dioxane (4.0 M, 17 mL, 68 mmol, 2.0 equiv) was added dropwise at 0° C. The reaction was allowed to stir 1 hr (0° C.→RT), then the sample was concentrated under vacuum and taken to the next step without further purification.

The residue was then dissolved in 3:1 MeOH—H₂O (150 mL), and the solution was adjusted to pH=10 with NaOH (1.0 N aqueous). Then di-tert-butyl dicarbonate (11.2 g, 51.4 mmol, 1.5 equiv) was added, and the reaction was stirred overnight at RT. After concentrating the sample under vacuum, H₂O (50 mL) was added, followed by citric acid (5% aqueous) to pH =3. The product was extracted with Et₂O (3×50 mL), and the combined organic phase was dried (MgSO₄), filtered, and concentrated to give 2.6 g (32% over three steps) of product as a 1:1 mixture of α,β- and β,γ-unsaturated acids. The material was taken on to the next step without further purification.

Step 4:

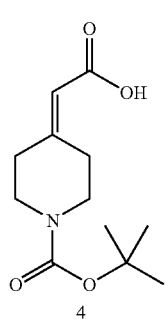

4

+

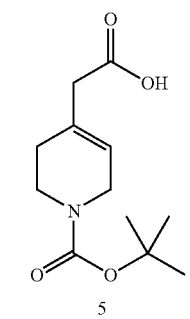

5

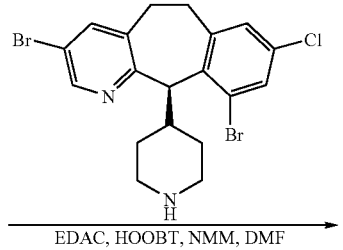
EDAC, HOOBT, NMM, DMF
→

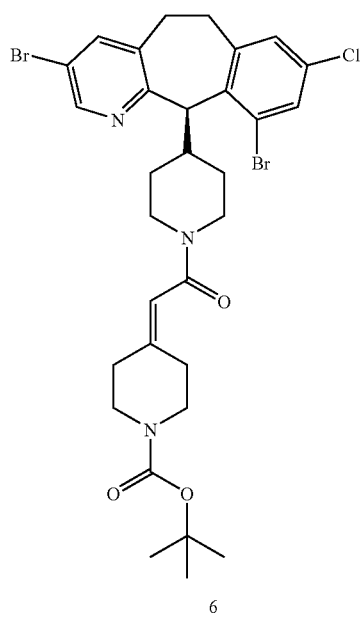

6

+

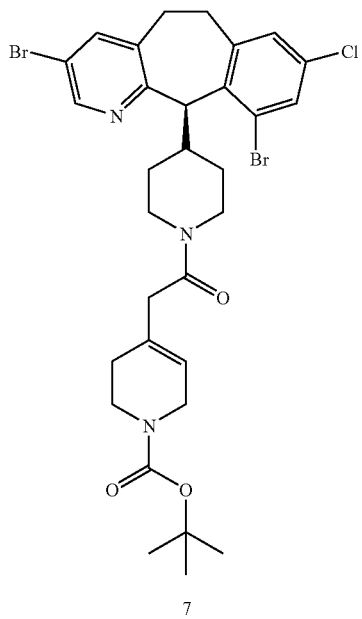

7

(+)-4-(3,10-Dibromo-8-chloro-6,11-dihydro-5H-benzo[5,6]cyclohepta[1,2-b]-pyridin-11(R)-yl)-piperidine (3.8 g, 8.1 mmol), a 1:1 mixture of Compound 4,1-tert-butoxycarbonylpiperidin-4-ylideneacetic acid, and Compound 5, 1-tert-butoxycarbonyl-1,2,5,6-tetrahydropyridineacetic acid, (2.61 g, 10.8 mmol, 1.3 equiv), 1-ethyl-3-(3-dimethylaminopropyl)carbodiimide (EDAC, 2.69 g, 14.1 mmol, 1.7 equiv), and 3-hydroxy-1,2,3-benzotriazin-4(3H)-one (HOOBT, 2.29 g, 1.7 equiv) were dissolved in DMF (100 mL). N-Methylmorpholine (9.5 mL, 8.8 g, 87 mmol, 10.7 equiv) was added and the mixture was stirred 50 hr at RT. NaHCO$_3$ (50 mL, saturated aqueous) was added, followed by ethyl acetate (100 mL) and H$_2$O (100 mL). The aqueous phase was extracted with ethyl acetate (6×30 mL), and the combined organic phase was dried (MgSO$_4$), filtered, and concentrated under vacuum. The residue was purified by silica gel chromatography (75:25 hexanes-ethyl acetate→25:75 hexanes-ethyl acetate) to give 3.66 g (65%) of coupled product as an off-white foamy solid. The material was carried into the next step as a 9:1 mixture of α,β- and β,γ-unsaturated amides, Compound 6, tert-Butyl(+)-4-[2-[4-(3,10-dibromo-8-chloro-6,11-dihydro-5H-benzo[5,6]cyclohepta[1,2-b]pyridin-11(R)-yl)-1-piperidinyl]-2-oxoethylidene]-1-piperidinecarboxylate, and Compound 7, tert-butyl (+)-4-[2-[4-(3,10-dibromo-8-chloro-6,11-dihydro-5H-benzo[5,6]cyclohepta[1,2-b]pyridin-11(R)-yl)-1-piperidinyl]-2-oxoethyl]-3,4-didehydro-1-piperidinecarboxylate (076483-151-29). Mp=112-125° C.

Step 5:
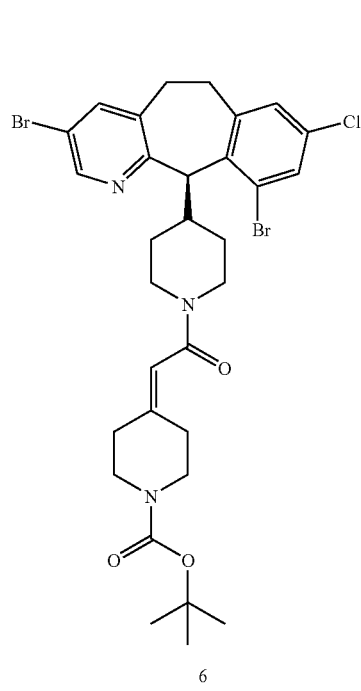
6
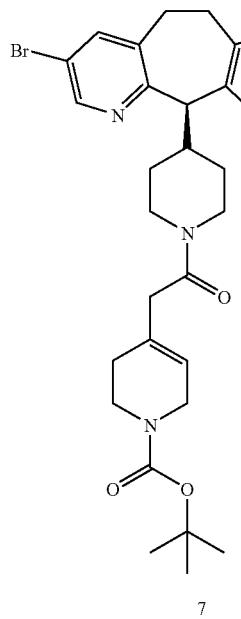
1) HCl, dioxane
2) TMSNCO, Et₃N →
7
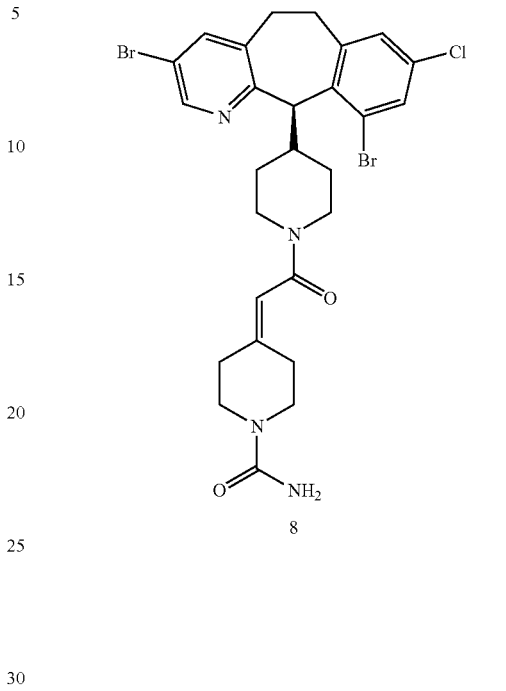
8
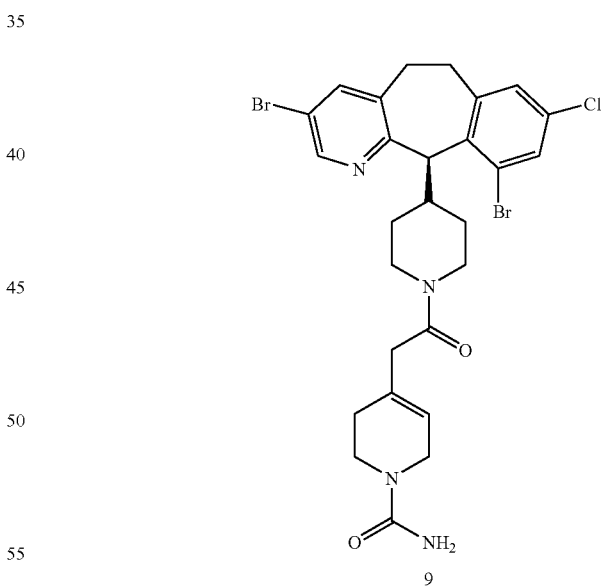
9
A 9:1 mixture of Compound 6, tert-Butyl (+)-4-[2-[4-(3, 10-dibromo-8-chloro-6,11-dihydro-5H-benzo[5,6]cyclohepta[1,2-b]pyridin-11(R)-yl)-1-piperidinyl]-2-oxoethylidene]-1-piperi-dinecarboxylate and Compound 7, tert-butyl (+)-4-[2-[4-(3,10-dibromo-8-chloro-6,11-dihydro-5H-benzo[5,6]cyclohepta[1,2-b]pyridin-11(R)-yl)-1-piperidinyl]-2-oxoethyl]-3,4-didehydro-1- piperidinecarboxylate was dissolved in $CH_2Cl_2$ (20 mL), and a solution of HCl in 1,4-dioxane (4.0 M, 4.6 mL, 18.4 mmol, 4.0 equiv) was added dropwise at 0° C. The mixture was stirred for 1 hr (0° C.→RT), and then concentrated under vacuum and taken to the next step without further purification.

The material was then dissolved in $CH_2Cl_2$ (25 mL), and $Et_3N$ (2.6 mL, 18.4 mmol, 4.0 equiv) was added. Trimethylsilyl isocyanate (2.1 g, 18.4 mmol, 4.0 equiv) was added dropwise to the solution at RT, and the reaction mixture was stirred for 1 hr. The reaction mixture was then concentrated under vacuum to give a white solid. The residue was purified by preparative TLC (85:15 $CH_2Cl_2$-MeOH) to give 900 mg (31%) of β,γ-unsaturated amide, (+)-4-[2-[4-(3,10-Dibromo-8-chloro-6,11-dihydro-5H-benzo[5,6]cyclohepta[1,2-b]pyridin-11(R)-yl]-1-piperidinyl]-2-oxoethylidene]-1-piperidinecarboxamide, Compound 9, (078017-013-22; major isomer) as an off-white foamy solid and 122 mg (4.2%) of α,β-unsaturated amide, (+)-4-[2-[4-(3,10-dibromo-8-chloro-6,11-dihydro-5H-benzo[5,6]cyclohepta[1,2-b]pyridin-11(R)-yl]-1-piperidinyl]-2-oxoethyl]-3,4-didehydro-1-piperidine-carboxamide, Compound 8, (078017-015-33; minor isomer) as a yellow solid. Mp (Compound 9, major isomer)=157-162° C.; mp (Compound 8, minor isomer) =167-171° C. HRMS (7.4:1 mix of Compound 9, major and Compound 8, minor isomers) m/z=637.0404.

Incubations Used to Prepare Compounds 10 and 11

Metabolites of Compound A having the structures of Compounds 10 and 11 were prepared in accordance with the procedures described in Examples 2-6 below.

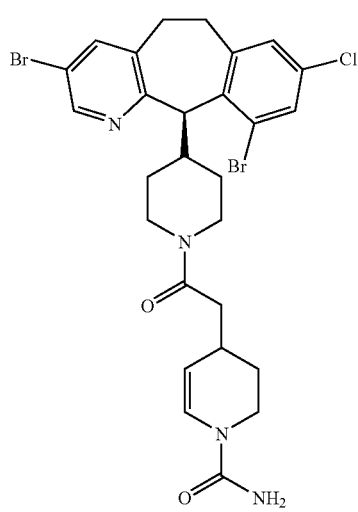

10

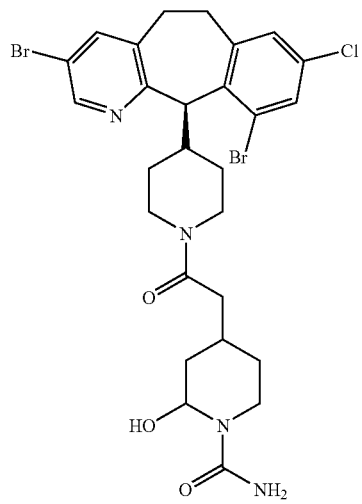

11

EXAMPLE 2

In vitro incubations of Compound A with hepatocytes from mouse, rat, monkey, and human were performed in 25-mL Erlenmeyer flasks containing 2 mL Waymouth Medium, either 2.54 μg (2 μM) or 63.8 μg (50 μM) Compound A (~20 μCi/mg), and 2×10⁶ cells under a blanket of oxygen:carbon dioxide 95:5 (v/v). Flasks were capped with rubber stoppers to maintain the composition of gases and placed in a 37° C. waterbath. Incubations were allowed to proceed for 5 hr with gentle shaking. Reactions were terminated by rapid freezing (−80° C.). Heat-inactivated hepatocytes were incubated in parallel with Compound A as the control.

EXAMPLE 3

Scaled-up production of Compound A metabolites was performed using rat liver microsomes from uninduced animals. Microsomes were incubated in a solution containing 1 nmol P450 per mL of 0.1 M phosphate buffer (pH 7.4). The incubation mixture also contained 10 mM $MgCl_2$, 5 mM glucose-6-phosphate, 1.5 units/mL glucose-6-phosphate dehydrogenase, 0.5 mM β-NADP (β-Nicotinamide Adenine Dinucleotide Phosphate) and 25 μM Compound A (~20 μCi/mg). Incubations were performed in four flasks, each containing 49.4 mL of the above mixture, and pre-incubated for 2 min at 37° C. without NADP. The reaction was initiated by the addition of NADP, incubated for 2 hr, and terminated by cooling the mixture in ice water. Solid phase extraction (SPE) was then performed on the combined incubation mixture that was directly applied in equally divided volumes to each of ten solid phase cartridges (tC18, 10 g absorbent).

These cartridges had been pre-washed with methanol and water. Drug-derived material was eluted with a total volume of 670 mL methanol (~70 mL per cartridge). Eluent was then evaporated under a nitrogen stream at 37° C. in a TurboVap LV workstation and the extract residue reconstituted in methanol for subsequent HPLC isolation.

EXAMPLE 4

An in vitro incubation was performed with human liver microsomes in the presence of a NADPH-generating system (5 mM glucose-6-phosphate, 1.5 units/ml glucose 6-phosphate dehydrogenese, 0.5 mM β-NADP) and 3 mM magnesium chloride for 30 min at 25 μM Compound A and 1 nmol/mL CYP450. Boiled microsomes were incubated under the same conditions as a control. After 30 min incubation, the samples were placed on ice and subjected to SPE. The methanol elutes were divided into 3 sets and one set of sample was analyzed by HPLC and the other 2 sets were analyzed by LC/MS and NMR. Afterward, methanol was replaced by acetonitrile to avoid a chemical reaction between the Compounds 10 or 11 and methanol.

The results of NMR analysis confirmed that Compound 10 had a double bond in the pendent piperidine ring. The structure of Compound 10 was completely identified by NMR following large-scale incubations with rat liver microsomes.

EXAMPLE 5

An in vitro incubation was performed with human CYP3A4 SUPERSOMES® in the presence of 3 mM magnesium chloride and an NADPH-generating system for 30 min at 25 μM of compound A, and 0.2 nmol/mL CYP450. Control insect microsomes were incubated under the same conditions as a control. After 30 min incubation, the samples were placed on ice and subjected to SPE. The methanol elutes were divided into two sets and one set of sample was analyzed by HPLC and other set by LC/MS.

The results of LC/MS analysis showed that the m/z of metabolite Compound 11 (RT~51.9 min) and metabolite Compound 10 (RT~61.6) were 653 and 635, respectively.

EXAMPLE 6

Recombinant human CYP3A4 enzymes (from Gentest and SPRI) were incubated separately using a constant amount of cytochrome P450 ("CYP") (0.2 nmol/mL) and 25 μM of Compound A. Incubations were performed in 60 mL potassium phosphate buffer (0.05 M, pH 7.4) for 30 min at 37° C. in air in the presence of 3 mM magnesium chloride and an NADPH-generating system. Reactions were initiated by addition of drug and terminated by cooling the incubation samples in a mixture of ice and water and immediately subjected to SPE (eluted with acetonitrile). Each sample was separately evaporated to dryness and analyzed by mass spectrometry (LC/MS and LC/MS/MS) and NMR.

Using appropriate starting materials and procedures as described above, and others known in the art, other compounds of formula (I) can be made.

Compound Isolation

The following isolations and purifications were performed and are illustrative of the types of isolation processes and purification processes that are applicable to the compounds of this invention. The following isolations are non-limiting examples of isolations that can be used to isolate the compounds of this invention. Other isolation processes that are known by those skilled in the art are equally applicable to isolate the compounds of this invention.

Isolation of Compound 10

Metabolites obtained from scaled-up production with rat liver microsomes were concentrated after SPE and separated by HPLC. The HPLC gradient elution method was optimized as shown in Table 1 below. The mobile phase consisted of 20 mM ammonium acetate adjusted to pH 6.0 using acetic acid and acetonitrile. The flow rate was set at 1.0 mL/min and the column temperature was maintained at 40° C. The eluent was monitored at 278 nm.

TABLE 1

| Time (min) | % 20 mM Ammonium Acetate (pH 6) | % Acetonitrile |
|---|---|---|
| 0 | 65 | 35 |
| 5 | 65 | 35 |
| 24 | 51 | 49 |
| 50 | 51 | 49 |

HPLC elution peaks of Compound 10 were manually collected from 39.2-41.2 min according to their UV absorption at 278 nm. The Compound 10 fraction was examined by LC-MS, where the molecular ions were detected as (M-2). The column collection was pooled and made into an NMR sample for analysis.

NMR Analysis of Metabolite Compound 10

The proton assignments of Compound A and Compound 10 are listed in Table 2. Most resonance assignments remained unchanged from the parent compound A except for two new resonances that were observed at 4.73 and 6.71 ppm. Their cross peak was observed in the proton-proton correlation spectrum. These two resonances are assigned to the olefinic protons at positions H-19' and H-20'. Protons at positions H-18, H-19, and H-20 were shifted downfield, due to formation of the double bond between C-19' and C-20'.

TABLE 2

The Proton NMR Chemical Shift Assignments for Compound A and Compound 10 in acetonitrile-$d_3$ at 20° C.

| Proton Position[a] | Compound A δ (ppm) | Compound 10 δ (ppm) |
|---|---|---|
| 2 | 8.41 | 8.41 |
| 4 | 7.69 | 7.69 |
| 5 | 3.31, 2.95 | 3.30, 2.95 |
| 6 | 3.65, 2.86 | 3.65, 2.85 |
| 7 | 7.29 | 7.28 |
| 9 | 7.56 | 7.56 |
| 11 | 4.81 | 4.81 |
| 12 | 2.52 | 2.52 |
| 13 | 1.49, 1.33, 1.21, 1.08 | 1.48, 1.33, 1.23, 1.13 |
| 14 | 4.45, 3.84, 2.86, 2.38 | 4.45, 3.84, 2.85, 2.38 |
| 17 | 2.23 | 2.28 |
| 18 | 1.87 | 2.59 |
| 19 | 1.66, 1.07 | 1.94, 1.49 |
| 20 | 3.85, 2.72 | 3.53, 3.36 |

TABLE 2-continued

The Proton NMR Chemical Shift Assignments for Compound A and
Compound 10 in acetonitrile-$d_3$ at 20° C.

| | | |
|---|---|---|
| 19' | —[b] | 4.73 |
| 20' | — | 6.71 |

[a]The proton positions are labeled on the structures shown below.
[b]Not applicable.

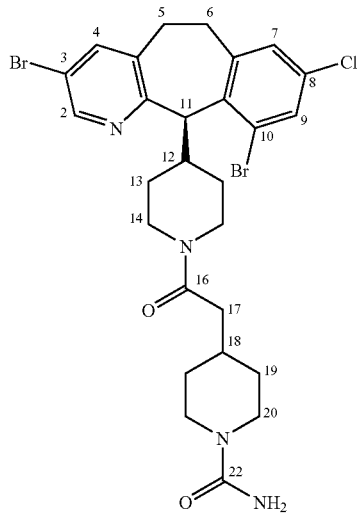

A

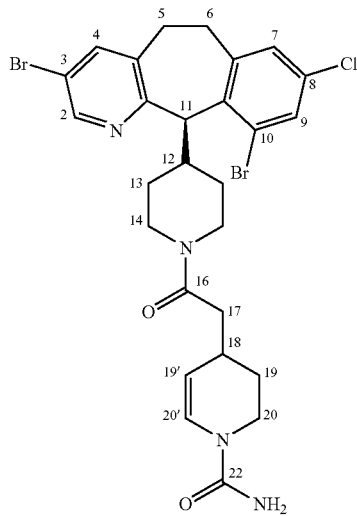

10

Isolation of Compound 11

Metabolite Compound 11 obtained from scaled-up incubation with recombinant CYP3A4 enzyme from BD Gentest (1E) were eluted by SPE and isolated by HPLC. The mobile phase consisted of 20 mM ammonium acetate adjusted to pH 6.0 using acetic acid and acetonitrile. The HPLC gradient elution method shown in Table 3 using a Luna Phenyl-hexyl semi-preparative column (5 μm, 250×10 mm i.d., Phenomenex, Inc., Torrance, Calif.). The flow rate was set at 4.0 mL/min and the column temperature at room temperature. The metabolite fraction was collected according to its UV absorbance at 278 nm. The fractions were pooled and made into an NMR sample in DMSO-$d_6$ for NMR data collection at 25° C.

TABLE 3

| Time (min) | % 20 mM Ammonium Acetate (pH 6) | % Acetonitrile |
|---|---|---|
| 0 | 65 | 35 |
| 10 | 65 | 35 |
| 20 | 54 | 46 |
| 30 | 51 | 49 |
| 50 | 51 | 49 |
| 52 | 5 | 95 |
| 60 | 5 | 95 |

NMR Analysis of Compound 11

The proton NMR assignments of Compound A and Compound 11 are listed in the following table. Most of the resonance assignments of Compound 11 remained unchanged from those of Compound A, except for the new proton resonance at 5.54 ppm The cross peaks of this resonance with H-19 and H-19' were observed in the proton-proton correlation spectrum. Its carbon chemical shift is found at 72.7 ppm, which is consistent with the formation of the secondary alcohol at position C-20'. Therefore the structure of Compound 11 is assigned as shown below, with a proton at H-20' substituted by a hydroxy on the pendent piperidine ring of Compound A.

TABLE 4

The Proton Chemical Shift Assignments for
Compound A and its Major Metabolite
Compound 11 in DMSO-$d_6$ at 25° C.

| Proton position[a] | Compound A δ (ppm) | Compound 11 δ (ppm) |
|---|---|---|
| 2 | 8.45 | 8.45 |
| 4 | 7.83 | 7.83 |
| 5 | 3.33, 2.94 | 3.33, 2.94 |
| 6 | 3.58, 2.93 | 3.58, 2.93 |
| 7 | 7.44 | 7.43 |
| 9 | 7.63 | 7.63 |
| 11 | 4.74 | 4.74 |
| 12 | 2.52 | 2.52 |
| 13 | 1.43, 1.00; 1.24, 1.00; 1.42, 1.21; 1.26, 1.10 | 1.41, 0.98; 1.24, 1.02; 1.43, 1.23; 1.25, 1.12 |
| 14 | 4.33, 2.39; 3.83, 2.87 | 4.34, 2.40; 3.82, 2.88 |
| 17 | 2.21 | 2.15 |
| 18 | 1.80 | 2.19 |
| 19 | 1.57, 0.99 | 1.61, 0.98 |
| 20 | 3.88, 2.61 | 3.60, 2.93 |
| 22-NH$_2$ | 5.83 | 5.90 |

TABLE 4-continued

The Proton Chemical Shift Assignments for
Compound A and its Major Metabolite
Compound 11 in DMSO-$d_6$ at 25° C.

| 19' | —[b] | 1.68, 1.11 |
| 20' | — | 5.54 |

[a]The proton positions are labeled on the structures shown below.
[b]Not applicable.

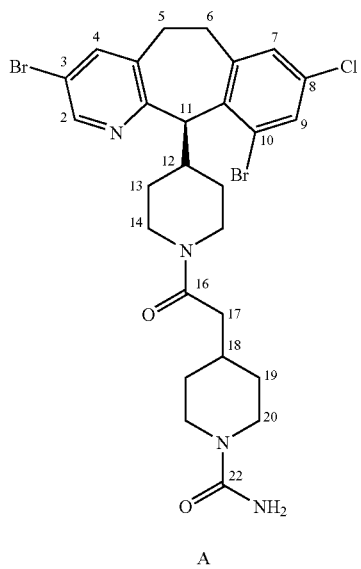

A

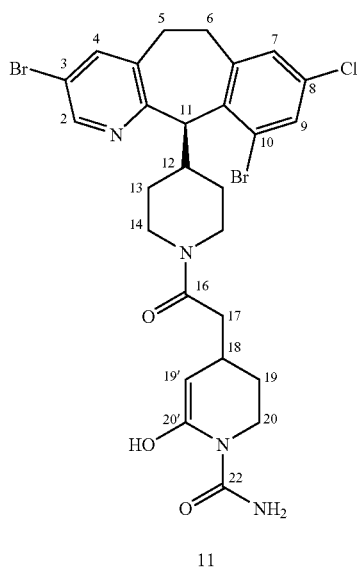

11

Assays

Activities in the (H-Ras) Farnesyl Transferase Inhibition Assay

In order to examine the pharmacological activity of Compound 10 and Compound 11, Compound A was incubated with high levels of recombinant expression of human CYP3A4 and human oxidoreductase in E.coli in 30-liter fermentors. Compound A was converted to Compound 11 and Compound 10 in 15-20% overall yield on a 1-liter scale. The metabolites were isolated following solid phase resin adsorption and purified by HPLC. The identities of both metabolites were confirmed by LC-MS/MS. A total of 4.45 mg of Compound 10 and 2.2 mg of Compound 11 were provided for biological activity evaluation.

The metabolites were examined by LC-MS (under conditions used for the pharmacological assay). The Compound 11 mixture was found to contain ~75% pure Compound 11 and ~25% pure Compound 10. The Compound 10 mixture was found to contain ~5% pure Compound 11 and ~95% pure Compound 10.

All of the above compounds exhibited the following $IC_{50}$ activity in the (H-Ras) Farnesyl Transferase Inhibition assay:

| Compound 8 | 2.6 nM |
| Compound 9 | 23.3 nM |
| Compound 11 (mixture) | 22.5 nM |
| Compound 10 (mixture) | 4.1 nM |
| Compound A (Control) | 2.4 nM |

Assay Conditions for (H-Ras) FPT

FPT activity was determined by measuring the transfer of [$^3$H] farnesyl from [$^3$H] farnesyl pyrophosphate to a biotinylated peptide derived from the C-terminus of H-Ras (biotin-CVLS). The reaction mixture contained 50 mM Tris pH 7.7, 5 mM $MgCl_2$, 5 μM $Z^{n++}$, 5 mM DTT, 0.1% Triton-X, 0.05 μM peptide, 0.03 nM purified human farnesyl protein transferase, 0.180 μM [$^3$H] farnesyl pyrophosphate, plus the indicated concentration of tricyclic compound or vehicle control in a total volume of 100 μL. The reaction mixture was incubated in a Vortemp shaking incubator at 37° C., 45 RPM for 60 minutes and stopped with 150 μL of 0.25 M EDTA containing 0.5% BSA and 1.3 mg/ml Streptavidin SPA beads. Radioactivity was measured in a Wallach 1450 Microbeta liquid scintillation counter. Percent inhibition was calculated relative to the vehicle control.

Pharmaceutical Preparations

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g., magnesium carbonate, magnesium stearate, talc, sugar, and lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. Water or water-propylene glycol solutions may be used for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms, which contain a compound of the invention. The scope of the invention in its pharmaceutical composition aspect is not to be limited by the examples provided.

Pharmaceutical Dosage Form Examples

TABLE 5

EXAMPLE A Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

TABLE 6

EXAMPLE B Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

Additional formulations, combinations of compounds that inhibit farnesyl protein transferase with other compounds (including anti-cancer agents), and methods of treatment using such formulations and/or combinations are disclosed in U.S. provisional application 60/498,509, which is herein incorporated as if fully set forth.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. An isolated form of a compound represented by the structural formula (I):

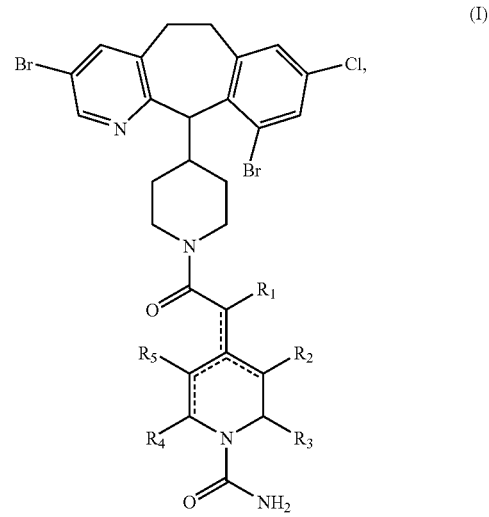

and pharmaceutically acceptable salts of the compound of formula (I), wherein:

$R_1$ is selected from the group consisting of H and =O;

$R_2$-$R_5$ can be the same or different, each being independently selected from the group consisting of H, —OH, halide, —$NH_2$ and =O; and, the combination solid-dashed lines independently represent either single bonds or double bonds, wherein the number of combination solid-dashed lines that are double bonds is not greater than 2, and when 2, the double bonds are not adjacent, and when 0, one of $R_1$-$R_5$ is not H.

2. The isolated form of the compound of claim 1 wherein $R_1$, $R_2$, $R_3$, and $R_5$ are each H, $R_4$ is selected from the group consisting of H and —OH, and the number of combination solid-dashed lines that are double bonds is not greater than 1.

3. The isolated form of the compound of claim 1 represented by the formula

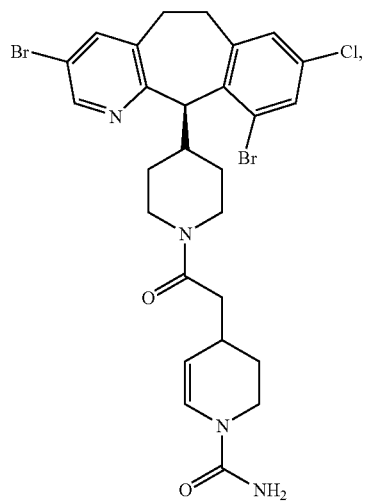

and pharmaceutically acceptable salts thereof.

4. The isolated form of the compound of claim 1 represented by the formula

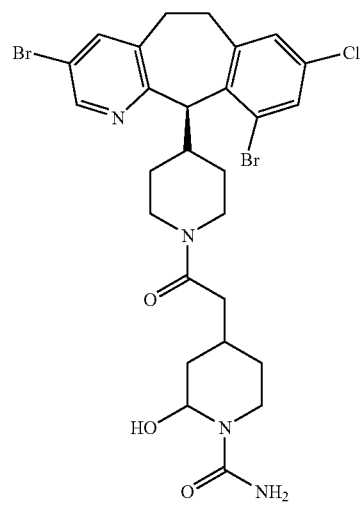

and pharmaceutically acceptable salts thereof.

5. The isolated form of the compound of claim 1 represented by the formula

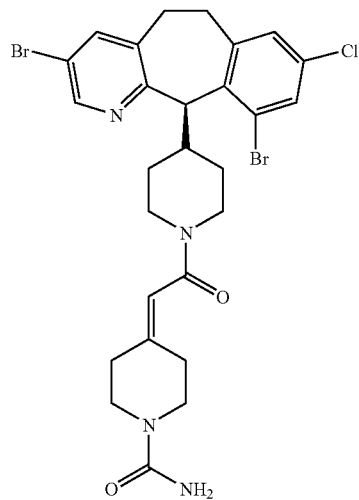

and pharmaceutically acceptable salts thereof.

6. The isolated form of the compound of claim 1 represented by the formula

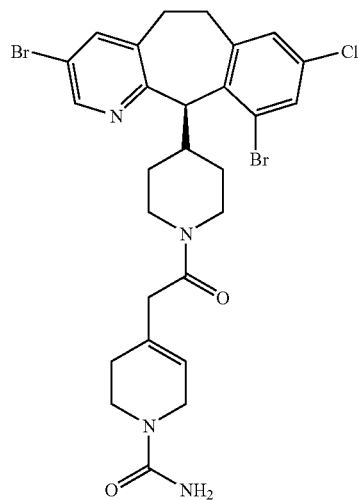

and pharmaceutically acceptable salts thereof.

7. A pharmaceutical composition comprising a therapeutically effective amount of a compound of claim 1 in combination with a pharmaceutically acceptable carrier.

* * * * *